United States Patent
Wahlberg

[19]

[11] Patent Number: 6,111,263
[45] Date of Patent: Aug. 29, 2000

[54] BUBBLE DETECTOR HAVING DETECTION DEPENDS ON POSITION OF IMPINGEMENT OF THE LIGHT BEAM

[75] Inventor: Andreas Wahlberg, Uppsala, Sweden

[73] Assignee: Octagon AB, Uppsala, Sweden

[21] Appl. No.: 09/142,147

[22] PCT Filed: Mar. 7, 1997

[86] PCT No.: PCT/SE97/00395

§ 371 Date: Sep. 2, 1998

§ 102(e) Date: Sep. 2, 1998

[87] PCT Pub. No.: WO97/33154

PCT Pub. Date: Sep. 12, 1997

[30] Foreign Application Priority Data

Mar. 7, 1996 [SE] Sweden ................................ 9600891

[51] Int. Cl.[7] .................................................. G01N 15/06
[52] U.S. Cl. ............................ 250/574; 250/577; 73/291
[58] Field of Search ................................. 250/574, 577, 250/573, 902, 906; 356/436, 437; 73/291, 293, 327; 128/766

[56] References Cited

U.S. PATENT DOCUMENTS 4,344,429  8/1982  Gupton et al. ........................... 250/574

FOREIGN PATENT DOCUMENTS

| 0 075 653 | 4/1983 | European Pat. Off. . |
| 0 121 848 | 10/1984 | European Pat. Off. . |
| 0 289 833 | 11/1988 | European Pat. Off. . |
| 0 706 044 | 4/1996 | European Pat. Off. . |
| 2 660 755 | 10/1991 | France . |

*Primary Examiner*—Que T. Le
*Attorney, Agent, or Firm*—Jacobson, Price, Holman & Stern, PLLC

[57] ABSTRACT

A bubble detector includes a conduit (1) through which a first fluid having a first refractive index is intended to flow, a light source (3) which directs a light beam (4; 41, 42) through a transparent conduit wall-part (12), through the conduit cavity and out through a second transparent conduit wall-part, and a detector means (5; 51, 52, 53) adapted to receive the light beam (4, 41) after the beam has passed through the conduit and the first fluid therein. The two opposing transparent wall-parts (12, 11) of the conduit (1) are trans-illuminated by the light beam and are essentially planar and parallel. The light source (3) is adapted to direct the beam (4) at an oblique angle ($\alpha$) to the proximal transparent wall-part (12) of the conduit (1), so that the light source will be broken into different paths (41, 42) depending on whether the beam passes the first fluid or a second conduit-carried fluid having a different refractive index, such as a bubble. The detector means (5; 53; 51, 52) is adapted to be impinged upon by the beam (4, 42) exiting from the conduit (1) irrespective of the refractive index of the fluids, and the detector means (5; 53; 51, 52) is adapted to deliver an output signal that is dependent on the position at which the beam (41, 42) impinges on the detector means, so as to enable the occurrence of bubbles in the first fluid to be identified.

5 Claims, 1 Drawing Sheet

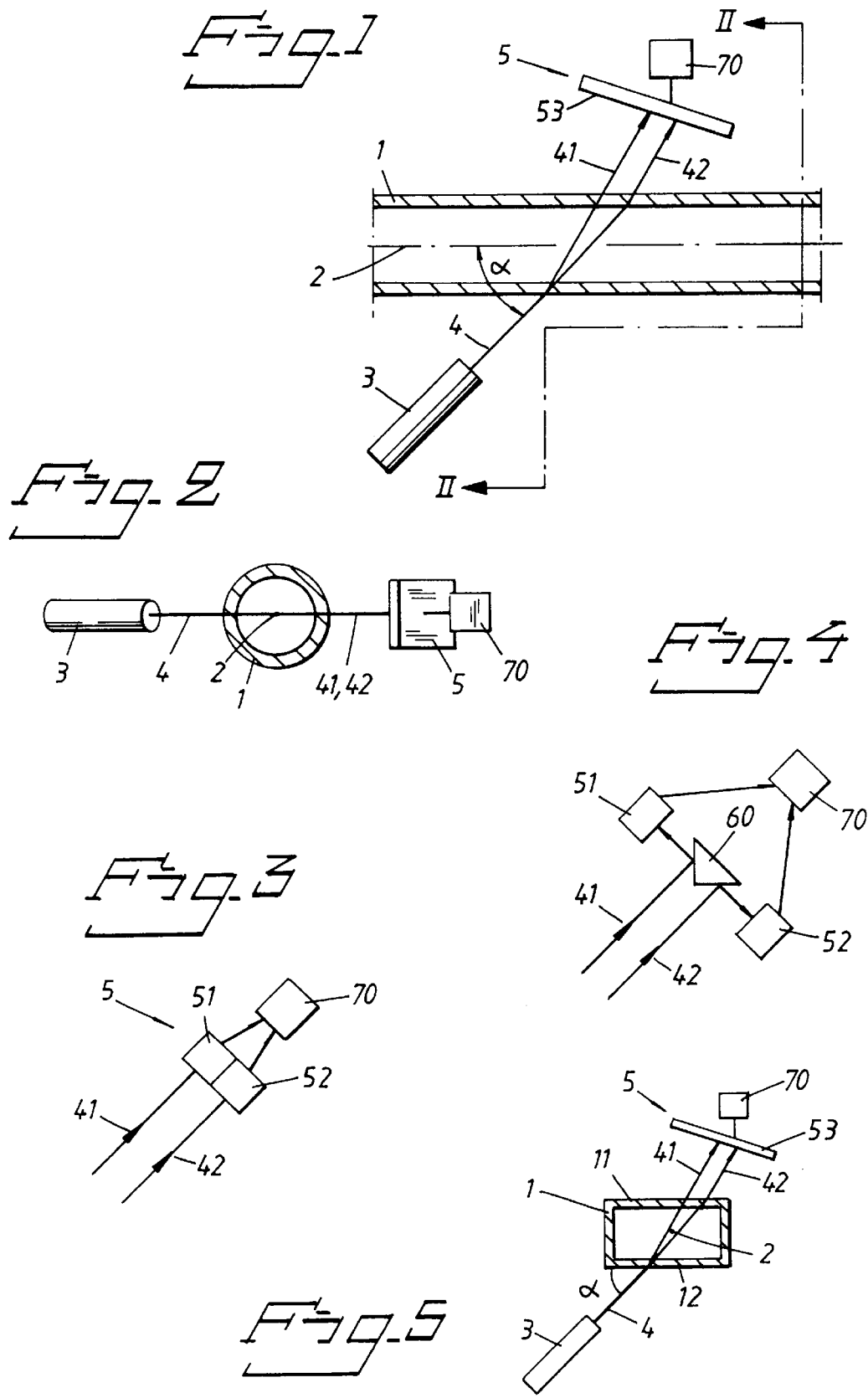

BUBBLE DETECTOR HAVING DETECTION DEPENDS ON POSITION OF IMPINGEMENT OF THE LIGHT BEAM

The invention relates to a bubble detector of the kind defined in the preamble of the following Claim 1.

BACKGROUND OF THE INVENTION

Earlier known technology is described in FR-A1-2 660 755, which discloses a bubble detector that includes a conduit through which a first fluid having a first refractive index passes, a light source which directs a light beam through a first transparent wall part of the conduit, through the conduit cavity, and out through a second transparent wall part of said conduit, and a detector means which receives the light beam after it has passed through the conduit and the first fluid present therein. It is also disclosed in FR-A1-2 660 755 that the light beam shall be directed in a plane normal to the axis of the circular-cylindrical conduit and be directed non-diametrically through said conduit. With this construction, it is necessary to accurately adjust the position and direction of the light source with respect to refractive index (the first fluid/liquid concerned), and the position of the detector must be adjusted to receive the light beam. This known arrangement presumes that the refractive index of the fluid is constant and will record error functions already at relatively small variations in the refractive index of the fluid. The reliability of the known arrangement is also relatively poor, because the presence of bubbles in the fluid is detected by non-detection of a light beam by the detector. When the light beam passes a bubble, the beam is split and spreads so that no clear light beam will leave the conduit.

Among other drawbacks with the known arrangement is that it gives no clear indication of malfunctioning of the main components.

The object of the present invention is to reduce or eliminate at least one of these drawbacks.

This object is achieved with a bubble detector according to the accompanying Claim 1.

SUMMARY OF THE INVENTION

The dependent Claims define further embodiments of the detector.

The invention is based on the fundamental concept that the two transparent conduit wall-parts that are trans-illuminated by the light beam shall be essentially flat and parallel and that the light beam is directed through the conduit at an oblique angle, e.g. 45 degrees, to the nearest plane of the trans-illuminated wall-part, so that the light beam will be broken into different paths depending on whether the beam in the conduit passes through the first fluid or through bubbles of a second fluid having a different refractive index. The detector means is therewith adapted to be impinged upon by the light beam exiting from the conduit independently of refractive index for the fluid or fluid mixture present between the two conduit wall-parts. The detector means is adapted to deliver an output signal that depends on the position at which the light beam meets the detector means, so as to enable the presence of bubbles of said second fluid in said first fluid to be identified by corresponding variations in the detector output signal.

In a preferred embodiment of the invention, the detector means includes a difference photodiode which delivers a signal that depends on the position at which the light beam meets the diode surface. A detector means of this nature can be readily calibrated; the first fluid, e.g. a liquid, can be passed through the conduit while ensuring that the first fluid is free from bubbles or the like. The signal that defines a bubble-free state of the first fluid is noted at the same time. A given deviation from this output signal will indicate a change in the refractive index of the medium in the conduit, that the detector means is malfunctioning, or that the alignment of the light source in relation to the conduit and/or the detector has been changed. Because the change in output signal is the result of a displacement in the distance of the position of contact of the light beam from the calibrating position, there will always be obtained an output signal from the detector means provided that the light source is operative and said arrangement has not broken down.

In a simplified variant of the invention, the detector means may include mutually separated, simple photodetectors instead of a difference photoelectrode. In this case, one photodetector is placed in a position in which it will be met by the light beam when passing through a bubble-free first fluid, and the other detector is placed in a position in which it will only be met by the light beam when said beam passes through a fluid in the conduit that has a different refractive index to said first fluid.

When the conduit is circular-cylindrical, the conditions whereby the conduit wall-parts trans-illuminated by the light beam are essentially planar and parallel can still be established, provided that it is ensured that the beam is narrow and cuts the conduit axis in its various refractive-index dependent paths. Thus, the path of the light beam will preferably lie in a plane that includes the conduit axis.

However, it will be obvious that the trans-illuminated wall-parts are preferably plane-parallel wall parts, so that the position at which the light beam meets said parts is not critical.

Because of the inventive concept, positive information is obtained from the detector means in the form of an output signal both when the conduit transports bubble-free fluid and when bubbles are present in the fluid flow, or when solely gas is present in the conduit.

Furthermore, information is obtained with regard to malfunctioning of the light source or malfunctioning of the detector means, by disappearance of the output signal.

Thus, the inventive detector means can be used to control the flow of fluid through the conduit and/or to trigger an alarm when bubbles appear, or when the detector output signal disappears completely.

The invention or forms thereof is defined in the following Claims.

An exemplifying embodiment of inventive arrangements will now be described with reference to the accompanying drawing.

BRIEF DESCRIPTION OF THE DRAWINGS

FIG. 1 is an axial sectional view of a schematically illustrated embodiment of the invention.

FIG. 2 is a sectional view taken on the line II—II in FIG. 1.

FIGS. 3 and 4 illustrates alternative embodiments of the inventive detector in the detector means.

FIG. 5 is a schematic illustration corresponding to FIG. 2 and shows the invention as applied to a conduit of rectangular cross-section.

DETAILED DESCRIPTION OF THE DRAWINGS

It will be apparent from FIGS. 1 and 2 that the inventive bubble detector includes a light permeable conduit 1, whose longitudinal axis is referenced 2. Liquid flows through the conduit 1 in the direction of its axis 2. The bubble detector functions to detect a gas bubble, such as an air bubble, in the liquid flow, said gas and liquid being assumed to have mutually different refractive indexes.

A light source 3 directs a light beam 4 through the conduit 1 at an oblique angle α to the axis 2. By "oblique" is meant an angle α that is greater than 0 and smaller than 90°, preferably an angle in the range of 30–60°, for instance about 45°. The conduit 1 shall be permeable to light at the two wall-parts 11, 12 through which the beam 4 passes.

The light beam 4 will take different paths through the conduit 1, depending on the refractive index of the medium located in the path of the light beam within the conduit 1. Thus, the light beam 4 will take the path 41 when the fluid in the conduit has essentially the same refractive index as the material from which the conduit 1 is made, as in the case when a liquid, such as water, flows through the conduit 1. The light beam 4 will take the path 42 in FIG. 1 when the fluid in the conduit has a refractive index that is significantly lower than that of a liquid, for instance when the fluid is air.

The conduit 1 has a cross-sectional size that corresponds to a bubble size that is considered to be dangerous or harmful, such that a bubble will be unable to pass through the conduit 1 by the side of the light beam 4; 41, 42.

It will be seen from FIG. 1 that the two beam paths 41, 42 are essentially parallel but separated when exiting from the conduit 1. The detector means 5 that receives the beams 41, 42 includes a detector 53, preferably a conventional difference photodiode, which delivers a signal whose magnitude depends on the position of impingement of the beam along the surface of the diode 53. Thus, the different output signals obtained from the positions of impingement of the beams 41, 42 can be easily distinguished from one another, and a further advantage afforded by a difference photodiode is that its position need not be adjusted in accordance with different refractive indexes of the liquid.

The bubble detector can thus be easily calibrated, by noting the output signal obtained in respect of a bubble-free liquid that has a known refractive index. When the characteristics of the detector are known, the refractive index of an unknown (bubble-free) fluid can be determined by the output signal obtained in respect thereof, this output signal thus being dependent on the position of impingement of the beam.

In the embodiment illustrated in FIGS. 1 and 2, the conduit 1 has a circular-cylindrical configuration. It is important in this case that the beams 4, 41, 42 intersect the conduit axis 2 so that the trans-illuminated wall-parts 11, 12 are planar and parallel in practice. However, when the conduit 1 is configured so as to have actually two flat plane-parallel wall-parts 11, 12 of uniform thickness, as illustrated in FIG. 5, the throughflow direction/axis 2 of the conduit 1 and the light beams 4, 41, 42 need not, of course, lie in a common plane, as will be evident from a study of FIG. 5.

FIG. 3 illustrates a simplified embodiment of the invention in which the detector means 5 includes two separated detectors 51, 52 that are positioned to receive the beam 41 and the beam 42 respectively. As before mentioned, it is difficult to adjust such a simplified detector means for liquids and bubbles of mutually different indexes. A prism 60 which functions to deflect the beams 41, 42 to the two detectors 51, 52 may be provided with the intention of obtaining a sharper definition between the two detectors 51, 52.

When the presence of a bubble or gas in the conduit is considered hazardous, it is obvious that the disappearance of one output signal from the detector corresponding to the signal 41 will constitute an alarm situation, and that an output signal corresponding to impingement of the beam 42 on the detector means will also constitute an alarm situation. The inventive arrangement thus obtains a significant redundancy. Because the detector means (or always at least one of the detectors 51, 52) will always deliver an output signal in response to an operable light source 3, there is immediately obtained an indication when the light source 3 malfunctions. An alarm indication is also given when the detector means 53 or one of the detectors 51, 52 has no output signal, this alarm indication being given immediately when the light source or the detector means malfunctions in some way or another. The illustrated arrangement includes a monitoring unit 20 which functions to control the transport of liquid through the conduit 1, for instance by closing a valve in the conduit in the event of an alarm indication. The unit may conveniently include an alarm means that is triggered in response to an alarm indication.

The invention finds general use in conjunction with the transportation of fluid through a conduit where it is important that fluid transportation can be stopped or that at least an alarm of some kind is generated when the refractive index of the fluid changes, such as when the fluid is a liquid that may not contain bubbles or be replaced with gas. The invention is therefore particularly useful in conjunction with the infusion of fluids to the blood circulation of the human body.

The conduit 1 will preferably have an inner diameter that is at maximum essentially equal to a bubble size that is considered hazardous, so that the beam 4 will always take the path 42 when a hazardous bubble passes through the conduit.

What is claimed is:

1. A bubble detector comprising a conduit (1) through which a first fluid having a first refractive index is intended to flow, a light source (3) that directs a light beam (4; 41, 42) through a transparent conduit wall-part (12) and through the conduit cavity and out through a second transparent conduit wall-part, and a detector means (5; 51, 52, 53) which is adapted to receive the light beam (4, 41) when the beam has passed through the conduit and the first fluid therein, characterized in that the two mutually opposite transparent wall-parts (12, 11) of the conduit (1) that are trans-illuminated by the light beam are essentially planar and parallel; in that the light source (3) is adapted to direct the light beam (4) at an oblique angle (α) to the proximal transparent conduit wall-part (12) so that the light beam is broken into different paths (41, 42) depending on whether the beam passes the first fluid or a second conduit-conducted fluid having another refractive index, such as a bubble; in that the detector means (5; 53; 51, 52) is adapted to be impinged upon by the light beam (4, 42) exiting from the conduit (1) irrespective of the refractive indexes of the fluids; and in that the detector means (5; 53; 51, 52) is adapted to deliver an output signal that depends on the position of impingement of the light beam (41, 42) on the detector means, so as to enable the occurrence of bubbles in the first fluid to be identified.

2. A detector according to claim 1, characterized in that the conduit is generally cylindrical, preferably circular-cylindrical; and in that the light beams (4, 41, 42) exiting from the light source (3) and the conduit axis (2) lie in a common plane.

3. A detector according to claim 1, characterized in that the detector means is adapted to trigger an alarm and/or to stop the transportation of the first fluid through the conduit (1) when the position of impingement of the light beam on the detector means deviates from the position of impingement that corresponds to the light beam passing through a bubble-free first fluid in the conduit.

4. A detector according to claim 1, characterized in that the detector means (5; 53; 51, 52) is coupled to monitoring logic that functions to trigger an alarm and/or stop transportation of fluid through the conduit (1) when the output signal disappears.

5. A detector according to claim 1, characterized in that the detector means is a difference photodiode (53) which delivers an output signal that is dependent on the position of impingement of the light beam (41, 42) on the diode's surface.

* * * * *